US00PP09136P

United States Patent [19]

Yanny

[11] Patent Number: Plant 9,136

[45] Date of Patent: May 16, 1995

[54] DWARF ASH TREE JOHNSON

[75] Inventor: Michael D. Yanny, Milwaukee, Wis.

[73] Assignee: J. Frank Schmidt & Son Co., Boring, Oreg.

[21] Appl. No.: 219,644

[22] Filed: Mar. 28, 1994

[51] Int. Cl.[6] ..... A01H 5/00

[52] U.S. Cl. ..... Plt./53.1

[58] Field of Search ..... Plt. 51.1, 53.1

*Primary Examiner*—James R. Feyrer

*Attorney, Agent, or Firm*—Klarquist Sparkman Campbell Leigh & Whinston

[57] ABSTRACT

A new and distinct variety of dwarf ash tree which I have named 'Johnson', characterized by its unusually small size and small leaves.

2 Drawing Sheets

The present invention relates to a new and distinct variety of dwarf ash tree which I have named 'Johnson.'

I discovered my new variety of tree growing as a chance seedling in a row of cultivated *Fraxinus pennsylvanica* in a nursery owned by Johnson's Nursery, Inc. and located in Waukesha County, Wis.

My attention was first directed to this tree because of its unusually small size and small leaves. On further inspection, I noticed that the tree seemed to be drawfed in the characteristics of height, spread, growth rate, internode length, and leaf size.

In comparing my new tree to other *Fraxinus pennsylvanica* trees of the same age growing under like conditions, I observed that my new variety appears to be approximately one-third to one-half size in all observable characteristics. The dwarf size of my new variety of ash tree makes it very suitable for use in planting sites where a small ultimate size is needed, such as small yards, and especially in locations where taller trees would interfere with overhead utility wires.

The original tree of my new variety is now nine years old, is about seven feet tall, and about four feet in width. Typical *Fraxinus pennsylvanica* seedlings of the same age are about 15 feet tall and about eight feet wide. I have propagated this tree by budding onto *Fraxinus pennsylvanica* seedlings at Johnson's Nursery, Inc., in Waukesha County, Wis., and I have also directed asexual propagation of my variety to be done by the same means at J. Frank Schmidt and Son Co. Nursery in Boring, Org.

Observation of the resulting progeny has proven the dwarf characteristics of my new variety to be firmly fixed. These observations have confirmed that my new variety represents a new and improved variety of ash tree as particularly evidenced by its reduced growth rate and dwarf stature. That is, the original tree of my new variety and all trees asexually propagated from it and from its clonal progeny are dwarf in nature, being about one-half or less in all dimensions when compared to typical *Franxinus pennsylvanica* trees growing under like conditions. Otherwise, the features of my new variety, insofar as I have been able to observe them as of this time, appear typical of those of *Fraxinus pennsylvanica* seedling trees.

The accompanying photographs depict the color of the leaves and tree of my new variety as nearly true as is reasonably possible to make the same in a colored illustration of this character.

BRIEF DESCRIPTION OF THE PHOTOGRAPHS

DETAILED DESCRIPTION

Figure 1:
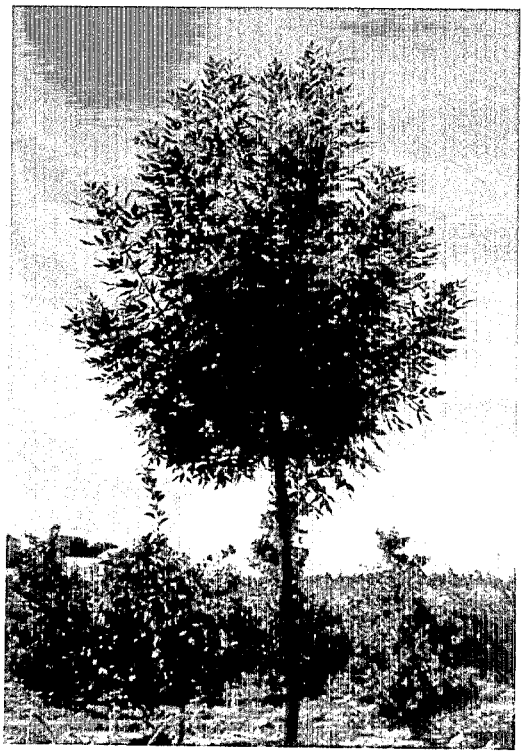
FIG. 1 shows a tree of my new variety which has been budded to *Fraxinus pennsylvanica* seedling understock.
Figure 2:
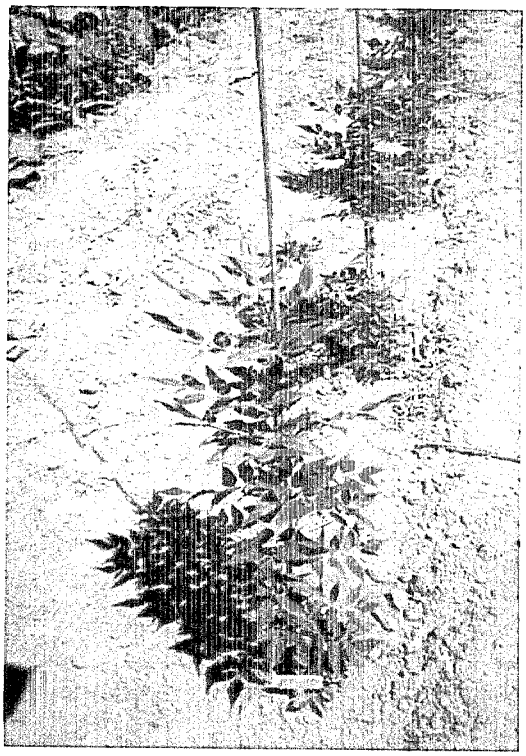
FIG. 2 shows a one-year old tree of my new variety budded to *Fraxinus pennsylvanica* seedling understock.
Figure 3:
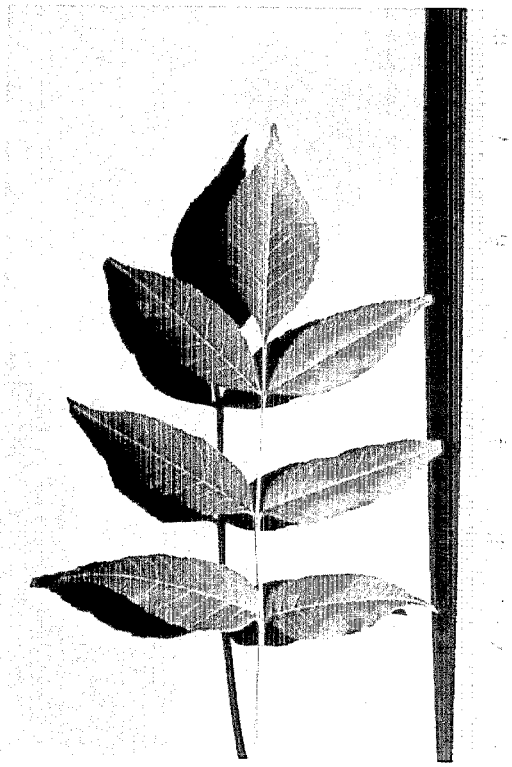
FIG. 3 shows a top view of a leaf from a tree of my new variety.
Figure 4:
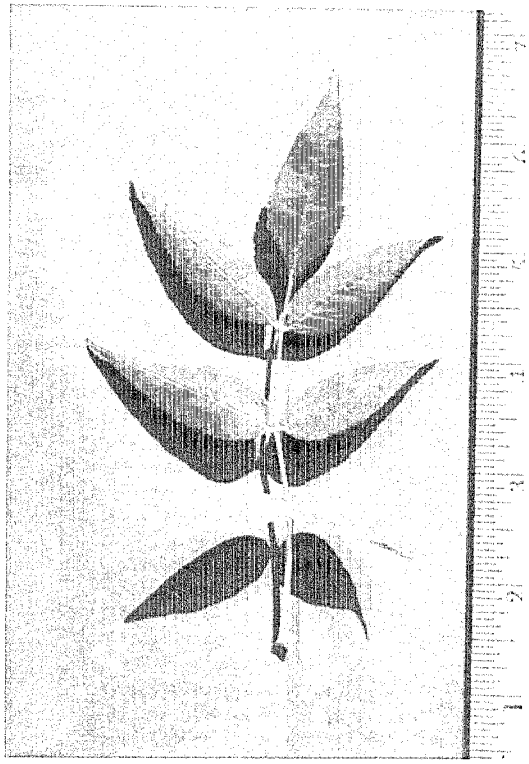
FIG. 4 shows a bottom view of a leaf from a tree of my new variety.
Figure 5:
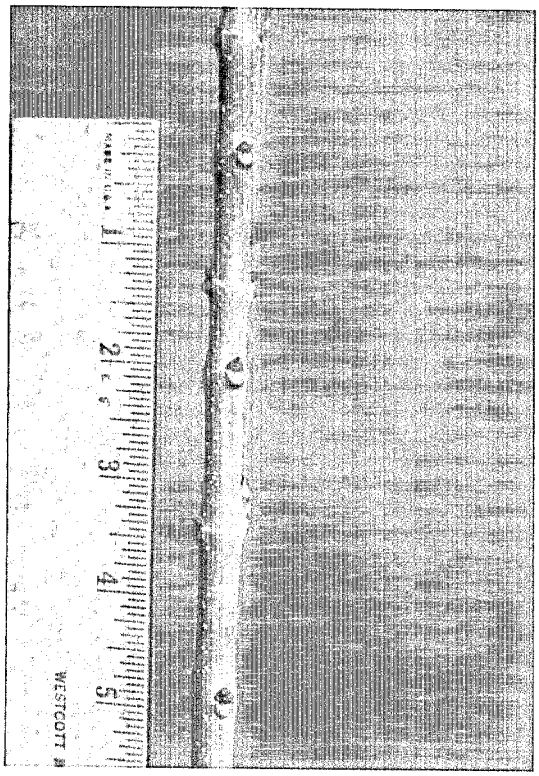
FIG. 5 shows a portion of a branch of a tree of my new variety.

The following comparison chart shows how my new variety of tree differs in growth characteristics from seedling *Fraxinus pennsylvanica* trees. To obtain the information depicted on the comparison chart, one-year old nursery trees, growing under like conditions in a nursery, were compared. The data found in the comparison chart is the average of 15 trees which were sampled. The leaf samples were taken from a point half-way down the stem from the terminal. The leaflet measurements were based on the third leaflet on the rachis, counting from the point of attachment to the stem. The internode length was measured halfway down the stem from the terminal.

Comparison Chart

| | 'Johnson' | Seedling |
|---|---|---|
| Height, 1 yr tree: | 58.6 cm | 186.7 cm |
| Internode length | 2.5 cm | 14.0 cm |
| Leaf length | 14.7 cm | 34.4 cm |
| Leaf width | 11.9 cm | 21.8 cm |
| Leaflet length | 6.2 cm | 12.6 cm |
| Leaflet width | 2.2 cm | 6.1 cm |

The following is a detailed description of my new variety of dwarf ash tree with color terminology in accordance with The Royal Horticultural Society Colour Chart (hereinafter R.H.S.), published by The Royal Horticultural Society of London.

Origination: Chance seedling of *Fraxinus pennsylvanica.*

Propagation: Holds to distinguishing characteristics through succeeding propagation by budding.

Locality where grown and observed:

Waukesha County, Wis., and Clackamas County, Oreg.

Tree shape: Dwarf tree with a densely branched round shape. The tree forms a dominant to weakly dominant central leader. Lateral branches emerge from the central trunk at wide crotch angles, typically between 60 degrees and 90 degrees at the point of attachment, forming a strong branch structure. The tree forms a symmetrical shape with little or no pruning. Because the shade created by the density of the canopy limits the growth of leaves on interior limbs, little pruning is required, although some thinning of branches may be desired.

Leaves: Opposite, pinnately compound, 7 to 9 leaflets per leaf. Leaves of vigorous new growth average 14.7 cm long by 11.9 cm wide. Leaflets are ovate to lanceolate, serrulate, with an acuminate tip. Leaflet size averages 6.2 cm long by 2.2 cm wide. Leaflets are glabrous on the upper surface and finely pubescent on the under surface, especially along the center vein. Leaflet serration is finely serrulate, with serrations extending from the apex to between 5 mm and 10 mm of the base of the leaflet.

Leaf surface color: R.H.S. Green 137A to Yellow-green 147A.

Leaf underside color: R.H.S. Yellow-green 147B.

Leaf surface fall color: R.H.S. Yellow-orange 20A

Buds: Finely tomentose, brown (R.H.S. Brown 200C to 200D). Terminal buds are pointed, lateral buds are rounded. Similar to typical *Fraxinus pennsylvanica* buds, except much smaller.

Stems: Rounded. Mature first year's growth in R.H.S. Grayed-green 197B. Internode length is very short compared to *Fraxinus pennsylvanica.*

Bark: Smooth on young plants. The bark of mature trees is rough with vertical cracking developing with age. Bark of a four year old tree is R.H.S. Grey 201A to Greyed-green 197A.

Flowers and fruit: The oldest trees have not yet flowered. Consequently, the flower and fruit characteristics are undetermined.

Growth rate: Very slow growing. The tree has been observed in Boring, Oreg., to grow at less than one-third the rate of the species as measured by terminal elongation. In addition to the height measurement shown in the above comparison chart, the following data was averaged for measurements of terminal elongation of ten trees of each category, growing side by side in a nursery in Boring, Oreg.

| | 'Johnson' | Seedling |
|---|---|---|
| 2 yr trees, Boring OR | 22 cm | 103 cm |
| 3 yr trees, Boring OR | 23 cm | 128 cm |

In addition, the original parent tree growing in Menomonee Falls, Wis., was observed and found to have grown 23 cm in height in the most recent year.

I claim:

1. A new and distinct variety of dwarf ash tree substantially as herein shown and described.

* * * * *